(12) United States Patent
Shahid

(10) Patent No.: US 11,547,333 B2
(45) Date of Patent: Jan. 10, 2023

(54) PHYSIOLOGICAL PARAMETER SENSING DEVICE

(71) Applicant: Aseeyah Shahid, Stone Mountain, GA (US)

(72) Inventor: Aseeyah Shahid, Stone Mountain, GA (US)

( * ) Notice: Subject to any disclaimer, the term of this patent is extended or adjusted under 35 U.S.C. 154(b) by 339 days.

(21) Appl. No.: 16/113,798

(22) Filed: Aug. 27, 2018

(65) Prior Publication Data

US 2019/0059800 A1 Feb. 28, 2019

Related U.S. Application Data

(60) Provisional application No. 62/550,635, filed on Aug. 27, 2017.

(51) Int. Cl.
| | | |
|---|---|---|
| *A61B 5/16* | (2006.01) | |
| *A61B 5/00* | (2006.01) | |
| *A61B 5/024* | (2006.01) | |
| *A61B 5/0205* | (2006.01) | |
| *A61B 5/01* | (2006.01) | |
| *A61B 5/021* | (2006.01) | |

(52) U.S. Cl.
CPC .......... *A61B 5/165* (2013.01); *A61B 5/02438* (2013.01); *A61B 5/681* (2013.01); *A61B 5/7246* (2013.01); *A61B 5/7278* (2013.01); *A61B 5/7282* (2013.01); *A61B 5/7405* (2013.01); *A61B 5/7445* (2013.01); *A61B 5/01* (2013.01); *A61B 5/021* (2013.01); *A61B 5/02055* (2013.01); *A61B 5/6898* (2013.01); *A61B 2560/0214* (2013.01); *A61B 2560/0242* (2013.01); *A61B 2560/0431* (2013.01); *A61B 2562/227* (2013.01)

(58) Field of Classification Search
CPC ..... A61B 5/165; A61B 5/02438; A61B 5/681; A61B 5/7246; A61B 5/7278; A61B 5/7282; A61B 5/7405; A61B 5/7445; A61B 5/01; A61B 5/02055; A61B 5/021; A61B 5/6898; A61B 2560/0214; A61B 2560/0242; A61B 2560/0431; A61B 2562/227; A61B 5/16; G09B 19/00
USPC ................................................ 434/236, 178
See application file for complete search history.

(56) References Cited

U.S. PATENT DOCUMENTS

| | | | | |
|---|---|---|---|---|
| 3,986,136 | A | * | 10/1976 | Hurlburt .................. A61B 5/16 331/78 |
| 2013/0120114 | A1 | * | 5/2013 | Gu ............................ G06F 7/02 340/5.83 |
| 2014/0085101 | A1 | * | 3/2014 | Rahman .................. G16H 40/67 340/870.01 |
| 2014/0324885 | A1 | * | 10/2014 | McKenzie ............ G06F 16/686 707/748 |
| 2014/0375465 | A1 | * | 12/2014 | Fenuccio .................. A61B 5/11 340/691.1 |
| 2015/0297109 | A1 | * | 10/2015 | Garten ................. A61B 5/0482 600/544 |
| 2017/0339484 | A1 | * | 11/2017 | Kim ...................... A61B 5/0478 |
| 2018/0050171 | A1 | * | 2/2018 | Tabert .................... A61B 5/486 |

(Continued)

*Primary Examiner* — Kurt Fernstrom
(74) *Attorney, Agent, or Firm* — Ballard Spahr LLP

(57) ABSTRACT

Systems and Methods for determining a physiological parameter are disclosed. The physiological sensing device can measure a physiological parameter, determine a mood based on the physiological parameter, and render one or more songs associated with the mood.

20 Claims, 4 Drawing Sheets

(56) References Cited

U.S. PATENT DOCUMENTS

| | | | | |
|---|---|---|---|---|
| 2019/0053770 A1* | 2/2019 | Liu | ..................... | A61B 5/746 |
| 2019/0307351 A1* | 10/2019 | Tan | ..................... | A61B 5/7445 |
| 2020/0035337 A1* | 1/2020 | Sohne | ................. | G08B 21/182 |
| 2020/0261000 A1* | 8/2020 | Kim | ................. | A61B 5/02055 |

* cited by examiner

FIG. 2A
FIG. 2B
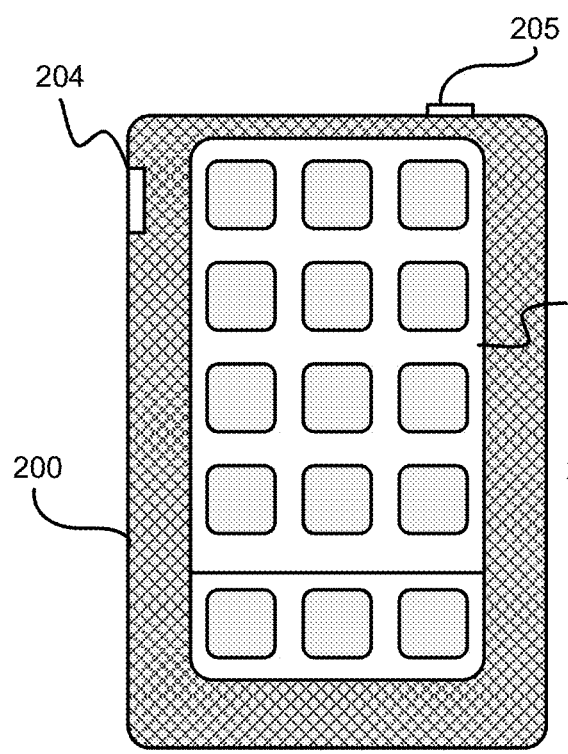
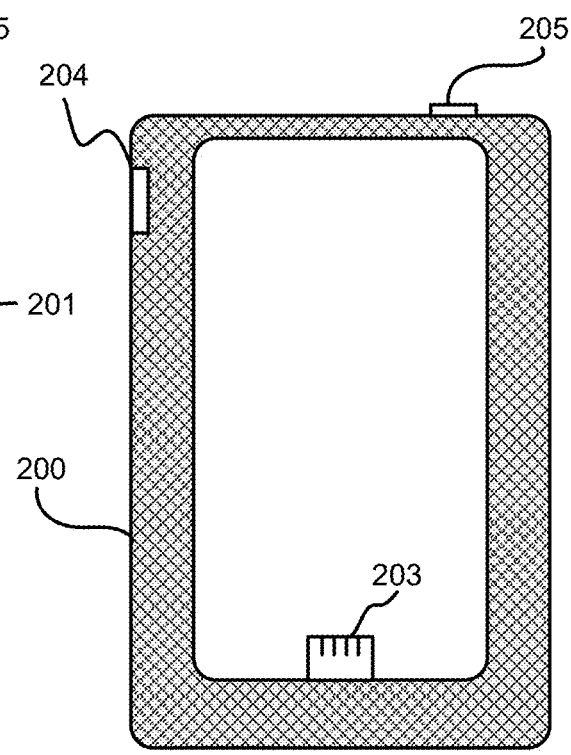

PHYSIOLOGICAL PARAMETER SENSING DEVICE

CROSS REFERENCE TO RELATED PATENT APPLICATION

This application claims priority to U.S. Provisional Application No. 62/550,635, filed Aug. 27, 2017, which is herein incorporated by reference in its entirety.

BACKGROUND

Consumers utilize heart rate monitors, pedometers, pulse oximeters to detect and/or sense what is commonly known as "physiological parameters." Physiological parameter sensing is an increasingly popular market segment, which has been, and continues to, steadily gaining market share over the last several years. Various types of personal sensors are known in the art. In general, such sensors are characterized by detecting a heart rate of a user, monitoring blood sugar levels of a user, or keeping track of steps of a user. Such devices are designed to allow users to monitor their activity and vitals, however, none of the devices actively seek to address a user's mood or psychological wellbeing. These and other shortcomings are addressed by the approaches set forth herein.

SUMMARY

It is to be understood that both the following general description and the following detailed description are exemplary and explanatory only and are not restrictive. In an aspect, provided are systems, methods, and devices comprising a hybrid electronic communication physiological parameter sensing device comprising an electronic communication device and a physiological parameter sensing device, wherein the physiological parameter sensing device is powered by at least one of a battery, charging, and a power system. In an aspect, the at least one of the battery, the charging, and the power system can be independent of the electronic communication device.

In another aspect, provided are methods comprising receiving a physiological parameter via a sensor in a device case, providing the physiological parameter to an application installed on a device contained in the device case, determining a mood state based on the physiological parameter, wherein the mood state has an associated color, selecting one or more songs based on the mood state, creating a playlist based on the selected one or more songs, and displaying the color associated with the mood state via a light source in the device case.

In a further aspect, provided are apparatuses comprising a housing, configured to receive a device, a physiological sensor for sensing a physiological parameter of a user, a light source for displaying a color, a power source configured to supply power to the physiological sensor, a communications unit configured for coupling to a device to exchange one or more of power and data, a processor configured to: receive a physiological parameter from the physiological sensor, provide the physiological parameter to an application installed on the device via the communication unit, receive a command indicating a color, and cause the light source to display the color.

In another aspect, provided are systems comprising a first device comprising a physiological sensor for sensing a physiological parameter of a user; a light source for displaying a color, a power source configured to supply power to the physiological sensor, a communications unit configured for coupling to a device to exchange one or more of power and data, a first processor configured to receive a physiological parameter via a sensor in a one or more devices, provide the physiological parameter to an application installed on one or more devices, and a second device comprising a power source, a communications unit configured for coupling to a device to exchange one or of power and data, and a second processor configured to determine a mood state based on the physiological parameter, wherein the mood state has an associated color. The second processor is also configured to select one or more songs based on the mood state, create a playlist based on the selected one or more songs, and provide a command to the first device to cause the light source of the first device to display a color.

Additional advantages will be set forth in part in the description which follows or may be learned by practice. The advantages will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments and together with the description, serve to explain the principles of the methods and systems:

FIG. 2A illustrates another exemplary hybrid electronic communication physiological parameter sensing device;

FIG. 2B illustrates another exemplary detachable physiological parameter sensing device;

DETAILED DESCRIPTION

Figure 1:
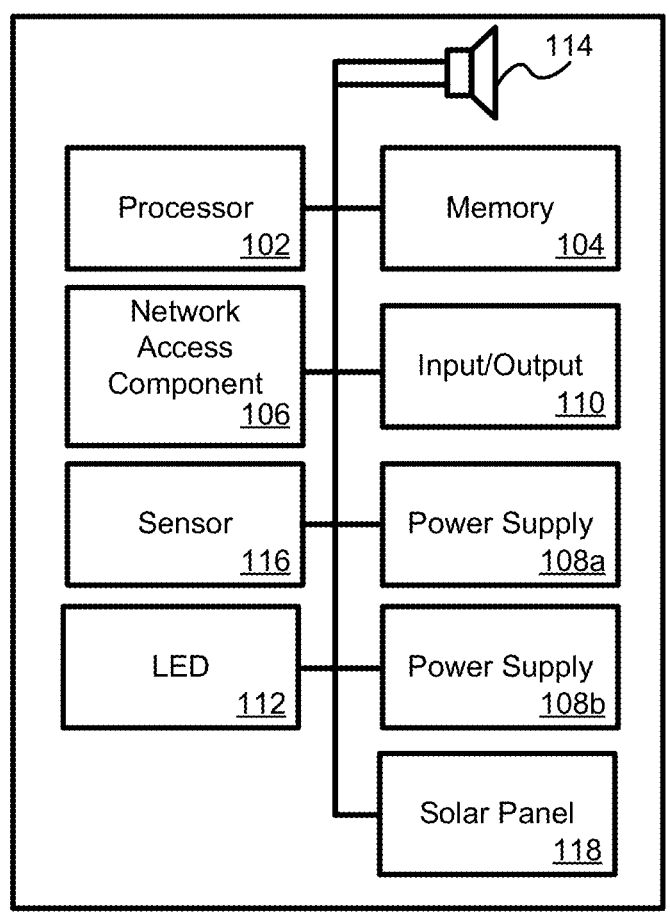
FIG. 1 illustrates a block diagram of an exemplary physiological parameter sensing device.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Various aspects are now described with reference to the drawings. In the following description, for purposes of explanation, numerous specific details are set forth in order to provide a thorough understanding of one or more aspects. It may be evident, however, that the various aspects may be practiced without these specific details. In other instances, well-known structures and devices are shown in block diagram form in order to facilitate describing these aspects.

Disclosed herein are exemplary embodiments for a physiological parameter sensing device. The physiological parameter sensing device can comprise one or more sensors configured for measuring at least one physiological parameter. The physiological parameter sensing device can comprise an input/output component configured for providing/transmitting the at least one physiological parameter to another device, such as an electronic communication device (e.g., a phone). In a further aspect, the physiological parameter sensing device can be integrated into an electronic communication device.

In an aspect, the physiological parameter sensing device can utilize a single battery or can utilize a plurality of batteries. For example, one battery can be for powering an electronic communication device (e.g., phone), and another battery can be for powering the physiological parameter sensing device. The one or more batteries can be rechargeable, for example, via one or more solar panels or via an external power supply. The one or more batteries can comprise a lithium-ion battery (e.g., thin film lithium ion batteries), a lithium ion polymer battery, a nickel-cadmium battery, a nickel metal hydride battery, a lead-acid battery, combinations thereof, and the like.

In an aspect, the one or more batteries can be utilized to power at least one of the electronic communication device, the physiological parameter sensing device, and/or an accessory device. In an aspect, the physiological parameter sensing device can be a "shuttle" type device that affixes to the electronic communication device to provide functionality, such as physiological parameter sensing functionality, increased battery power functionality, and the like. For example, the physiological parameter sensing device can provide power to the electronic communication device to which the physiological parameter sensing device is attached. Stated differently, the physiological parameter sensing device can have the capability to be a backup power supply for the electronic communication device.

FIG. 1 is a block diagram of an exemplary physiological parameter sensing device 100 as described herein. The physiological parameter sensing device 100 can be any device capable of sensing a physiological parameter of a user of the device. For example, the physiological parameter sensing device 100 can be an activity tracker, a pedometer, a smart watch, a case for an electronic communication device, an integral part of an electronic communication device, and the like. The physiological parameter sensing device 100 can comprise any suitable housing for enclosing and protecting the various components disclosed herein.

In an aspect, the physiological parameter sensing device 100 can comprise a processor 102. The processor 102 can be, or can comprise, any suitable microprocessor or microcontroller, for example, a low-power application-specific controller (ASIC) and/or a field programmable gate array (FPGA) designed or programmed specifically for the task of controlling a device as described herein. The processor 102 can also be a general purpose central processing unit (CPU), for example, one based on 80×86 architecture as designed by Intel™ or AMD™, or a system-on-a-chip as designed by ARM™. The processor 102 can be coupled (e.g., communicatively, operatively, etc . . . ) to auxiliary devices or modules of the physiological parameter sensing device 100 using a bus or other coupling. The processor 102 can be configured to execute instructions stored in a memory 104. For example, the processor 102 can execute program code or program instructions stored within the memory 104.

The physiological parameter sensing device 100 can comprise the memory 104 coupled to the processor 102. The memory 104 can be any type of volatile or non-volatile memory such as a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like. The memory 104 can comprise a random access memory (RAM) configured for storing program instructions and data for execution or processing by the processor 102 during control of the physiological parameter sensing device 100. The memory 104 can also comprise long-term memory. For example, when the physiological parameter sensing device 100 is powered off or in an inactive state, program instructions and data can be stored in a long-term memory, a non-volatile magnetic optical, or electronic memory storage device. The memory 104 can comprise a non-transitory computer-readable medium storing program instructions that, when executed by the processor 102, cause the physiological parameter sensing device 100 to perform all or part of one or more methods and/or operations described herein. Program instructions can be written in any suitable language, for example, C, C++, C# or the Java™, and compiled to produce machine-language code for execution by the processor 102. Further, the program instructions can be a combination of software and/or firmware.

In an aspect, the physiological parameter sensing device 100 can comprise a network access component 106 allowing the physiological parameter sensing device 100 to be communicatively coupled to a communications network. The communications network can be a wired or a wireless network. For example, the communications network can be a local area network (LAN), a wide area network (WAN), a wireless network (Wi-Fi), and so forth. One or more computing devices can be communicatively coupled via the communications network.

The physiological parameter sensing device 100 can communicate via the network access component 106 to the communications network. For example, the physiological parameter sensing device 100 can be configured to share data with the one or more other computing devices via the network access component 106. The shared data can comprise, for example, usage data and/or operational data of the physiological parameter sensing device 100, a status of the physiological parameter sensing device 100, a status and/or operating condition of one or more of the components of the physiological parameter sensing device 100, and/or any other data. For example, the physiological parameter sensing device 100 can communicate with a computing device (e.g., a smartphone, a tablet, a computer, etc.) communicatively coupled with the physiological parameter sensing device 100 via the network access component 106. The physiological parameter sensing device 100 can use the computing device as an output of the physiological parameter sensing device 100. As an example, the physiological parameter sensing device 100 can communicate data to the computing device for the computing device to display to a user of the computing device, such as, a mood of the user, a song option for the user, a playlist option for the user, and so forth. Further, the computing device can display to the user settings and/or options for operating the physiological parameter sensing device 100.

The physiological parameter sensing device 100 can also be configured to receive control instructions from a computing device (e.g., a smartphone, a tablet, a computer, etc.) via the network access component 106. The computing device can be a smartphone, a smart watch, a smart lighting device (e.g., a smart lightbulb), a smart speaker, a tablet, a laptop, and combinations thereof The physiological parameter sensing device 100 can receive data related to the operation of the physiological parameter sensing device 100 via the network access component 106. For example, a computing device can transmit operational data to the physiological parameter sensing device 100 via a network that the network access component 106 is communicatively coupled with. The operational data can include operating parameters, operational instructions, settings, and so forth for operating the physiological parameter sensing device 100. As an example, the computing device can be communicatively coupled with the physiological parameter sensing device 100, and the computing device can provide the physiological parameter sensing device 100 with operational parameters and/or settings for the physiological parameter sensing device 100. The computing device can display the operational settings of the physiological parameter sensing device 100 to the user of the computing device. The user can then interact with the computing device to adjust the settings of the physiological parameter sensing device 100. The computing device will then in turn transmit the settings to the physiological parameter sensing device 100 via the network access device 106. After receiving the settings from the computing device, the physiological parameter sensing device 100 can update the operational settings for the physiological parameter sensing device 100. In this manner, a computing device external to the physiological parameter sensing device 100 can control operation of the physiological parameter sensing device 100. While controlling operation of the physiological parameter sensing device 100 has been described with regards to the network access device 106 for ease of explanation, a person skilled in the art would appreciate that similar functionality can occur via the input/output 110 as described in further detail below.

The physiological parameter sensing device 100 can comprise a power supply 108a.

The power supply 108a can be associated with a computing device external to the physiological parameter sensing device 100. For example, the power supply 108a can be a battery of a smartphone that the physiological parameter sensing device 100 is coupled with. The power supply 108a can comprise one or more batteries and/or other power storage devices (e.g., capacitors). The power supply 108a can also comprise a port for connecting to an external power supply. For example, the port can be a Universal Serial Bus (USB) port such as USB-C, or similar port, capable of connecting to an external battery, a smartphone, a computing device, and/or a power outlet. The one or more batteries can be rechargeable. In an aspect, the port can be used to recharge the one or more batteries of the power supply 108a. The one or more batteries can comprise a lithium-ion battery (e.g., thin film lithium ion batteries), a lithium ion polymer battery, a nickel-cadmium battery, a nickel metal hydride battery, a lead-acid battery, combinations thereof, and the like. For example, an external power supply can supply power to the physiological parameter sensing device 100 via the power supply 108a. The power supply 108a can store at least a portion of the power from the external power supply. In an aspect, the physiological parameter sensing device 100 is a phone case, and the external power supply is one or more batteries that can be utilized to power at least one of a smartphone, a computing device, and/or the physiological parameter sensing device 100. As an example, the external power supply can be a battery of the smartphone with which the physiological parameter sensing device 100 is connected to. In an aspect, the physiological parameter sensing device 100 can be a "shuttle" type device that affixes to a smartphone or a computing device to provide functionality, such as physiological parameter sensing functionality, increased battery power functionality, and the like.

In an aspect, the power supply 108a can be configured to supply power exclusively to components that are not directly associated with physiological parameter sensing functionality. For example, the power supply 108a can be configured to exclusively provide power to the processor 102, the memory 104, the network access component 106, and an input/output 110 (among other components). Thus, the power supply 108a can be configured to not provide power to a sensor 116. In another aspect, the power supply 108a can be configured to supply power to all components of the physiological parameter sensing device 100, including the sensor 116.

In another aspect, the physiological parameter sensing device 100 can comprise a power supply 108b. For example, the power supply 108b can be a power supply internal to the physiological parameter sensing device 100. The power supply 108b can comprise one or more batteries and/or other power storage devices (e.g., a capacitor). The power supply 108b can also comprise a port for connecting to an external power supply. For example, the port can be a USB-C, or similar port, capable of connecting to an external battery, a smartphone, a computing device, and/or a power outlet. The one or more batteries can be rechargeable. In an aspect, the port can be used to recharge the one or more batteries of the power supply 108b. The power supply 108b can be configured to supply power exclusively to components that are directly associated with physiological parameter sensing functionality. For example, the power supply 108b can be configured to exclusively provide power to the sensor 116 (among other components). Thus, the power supply 108b can be configured to not provide power to the processor 102, the memory 104, the network access component 106, and the input/output 110 (among other components). In another aspect, the power supply 108b can be configured to supply power to all components of the physiological parameter sensing device 100. In another aspect, the power supply 108b can serve as a backup power source for the physiological parameter sensing device 100 in the event the power supply 108a fails and/or has insufficient energy to power the physiological parameter sensing device 100. While the power supplies 108a and 108b have been described as separate power supplies for ease of explanation, a person skilled in the art would appreciate that the physiological parameter sensing device 100 can comprise one power supply, or more than two power supplies, and should not be limited to the exemplary embodiment shown in FIG. 1.

In an aspect, one or more charging methods can be used to charge the power supplies 108a and 108b. For example, the charging methods can include wireless charging (e.g., inductive charging and/or conductive charging), supplying a constant DC or pulsed DC power source to battery being charged, a motion-powered charger, a pulse charger, a solar charger, a wind charger, a Universal Serial Bus (USB) charger, combinations thereof, and the like. For example, the physiological parameter sensing device 100 can comprise one or more solar panels 118. The solar panels 118 can be used to capture solar energy and provide power to the power supplies 108a and 108b. Thus, the solar panels 118 can be used to recharge batteries associated with the power supplies 108a and 108b.

In an aspect, the physiological parameter sensing device 100 can also comprise an input/output 110 coupled to one or more of the processor 102, the sensor 116, the network access component 106, any other electronic component of the physiological parameter sensing device 100 (e.g., an input device, a display, etc.), and/or an external computing device. Input can be received from a user or another device via the input/output 100. Further, output can be provided to a user or another device via the input/output 110. The input/output 110 can be communicatively coupled with any combination of input and/or output devices such as buttons, knobs, a keyboard, a touchscreen, a display, light-emitting elements, a speaker, another computing device (e.g., a computer, a smartphone, a tablet, a server, etc.) and/or the like.

In an aspect, the input/output 110 can comprise an interface port such as a wired interface. For example, the input/output 110 can be a serial port, a Universal Serial Bus (USB) port, an Ethernet port, or other suitable wired connection. The input/output 110 can also comprise one or more of, a USB connection of any type, a dock connector (e.g., 20-24-30 pin connectors, a Lightning Port connection, etc.), Portable Digital Media Interface, and the like. An input/output port of a smartphone and the input/output 110 can be used to pass power and/or data between a smartphone and the physiological parameter sensing device 100. The input/output 110 can comprise a wireless interface (not shown), for example a transceiver using any suitable wireless protocol, for example Wi-Fi, Bluetooth®, infrared, or other wireless standard. For example, the physiological parameter sensing device 100 can transmit data to, and receive data from, a computing (e.g., a smartphone, a tablet, a server, etc.) via the input/output 110. As an example, the computing device can comprise a user interface that a user of the computing device can interact with. The computing device can transmit data to the physiological parameter sensing device 100 via the input/output 110. As another example, the physiological parameter sensing device 100 can use the input/output 110 to provide the computing device with an interface to display to the user. The interface can comprise operational settings of the physiological parameter sensing device 100, as well as other data such as a mood color, a song, and/or a playlist. Thus, the input/output 110 can allow the physiological parameter sensing device 100 to communicate with a computing device.

The physiological parameter sensing device 100 can comprise a Light Emitting Diode (LED) 112. The LED 112 can output a plurality of colors. For example, the physiological parameter sensing device 100 can determine a mood of a user associated with the physiological parameter sensing device 100, and the physiological parameter sensing device 100 can instruct to the LED 112 to output a specific color of light based on the user's mood. As an example, the physiological parameter sensing device 100 can determine that the user is angry. Based on the determination that the user is angry, the physiological parameter sensing device 100 can instruct the LED 112 to output the color red, as the color red can be generally associated with anger. As another example, the physiological parameter sensing device 100 can change instruct the LED 112 to changes the output of the LED 112 if the mood of the user changes. Going back to the previous example, if the user changes from angry to calm, the physiological parameter sensing device 100 can instruct the LED 112 to change the output from the color red to the color blue, as the color blue is can be generally associated as a calming color. While a single LED 112 is shown for ease of explanation, a person skilled in the art would appreciate that the physiological parameter sensing device 100 can comprise any number of LEDs 112.

The physiological parameter sensing device 100 can comprise a speaker 114. The speaker 114 can be configured to output an audio signal. For example, the speaker 114 can output a song or audible tone. In an aspect, the speaker 114 can be configured to provide audio to a single user. For example, the speaker 114 can be comprise headphones, earphones, earpieces, ear buds, or the like that a user wears. In an aspect, the speaker 114 can be configured to present audible media. In an aspect, the media can be stored locally, in the memory 104. In an aspect, the media can comprise an audio component. For example, the speaker 114 can play music. The music can be determined by the physiological parameter sensing device 100. As an example, the physiological parameter sensing device 100 can select the music based on a mood of the user. As another example, the physiological parameter sensing device 100 can transmit a signal via the input/output 110 to a computing device. In response to receiving the signal, the computing device can play the audio signal. While a single speaker 114 is shown for ease of explanation, a person skilled in the art would appreciate that the physiological parameter sensing device 100 can have more than one speaker.

As shown, the physiological parameter sensing device 100 has a sensor 116. The sensor 116 can be configured to measure physiological parameters (e.g., an ambient temperature, a temperature of a user, a heart rate of a user, blood pressure of a user, blood oxygen levels of a user, etc.). The sensor 116 can comprise one or more of, a heart rate sensor, a thermal sensor, a pulse oximeter, an electrical sensor, and combinations thereof. For example, the sensor 116 can comprise a heart rate sensor configured to detect the pulse through the skin. The sensor 116 can also comprise a thermal sensor configured to detect an ambient temperature, a temperature of a user, heat, heat flow, entropy, heat capacity, combinations thereof, and the like. The sensor 116 can further comprise a pulse oximeter configured to determine the oxygen saturation of the blood of a user. Additionally, the sensor 116 can comprise an electrical sensor configured to detect charge, current, voltage, resistance, conductance, capacitance, inductance, dielectric permittivity, polarization and frequency.

The physiological parameter sensing device 100 can automatically determine a physiological parameter when a user interacts with the sensor 116. For example, the sensor 116 may be a heart rate monitor. When a user interacts with the sensor 116 (e.g., the user physically contacts the sensor 116 with the user's skin), the physiological parameter sensing device 100 can detect that the user is interacting with the sensor 116. The physiological parameter sensing device 100 will then monitor and record any output from the sensor 116. In this manner, the user of the physiological parameter sensing device 100 does not need to manually turn on and/or activate the sensor 116 for the physiological parameter sensing device 100 to determine the physiological parameter.

The physiological parameter sensing device 100 can use the data from the sensor 116 to determine the mood (e.g., the mood state) of the user. For example, the sensor 116 can provide data indicative of the physiological parameter to the processor 102. The processor 102 can in turn determine a value of the physiological parameter based on the data provided by the sensor 116. For example, the processor 102 can compare the data received from the sensor 116 to a mood index. The mood index can correlate a measured physiological parameter to a specific mood and/or mood state of a user. For example, if the sensor 116 is a heart rate monitor, and the sensor 116 provides a beats-per-minute (BPM) reading of 140 BPM, the processor 102 can determine that the high BPM reading correlates to stress and/or anger. Thus, the processor 102 can determine that the user has a stressed and/or angered mood state.

The processor 102 may make the determination of the mood state based on a baseline of the user. For example, the user may have a normal resting heart rate of 80 BPM. Thus, the processor 102 can use the baseline of 80 BPM to determine whether the user's heartrate is normal, above normal, and/or below normal. Stated differently, the physiological parameter sensing device 100 can be calibrated to each individual user to ensure the mood states are properly determined. In this manner, the physiological parameter sensing device 100 is capable of providing a personalized mood reading to the user based on the physical characteristics of the user.

Exemplary mood states include, but are not limited to happy, excited, sad, depressed, and angry. A color can be associated with each mood state. For example, if a user has a sad mood state, the color blue can be associated with the mood state because the color blue is generally associated with being sad. The processor 102 can cause the LED 112 to display the color associated with the determined mood state of the user. In an aspect, the LED 112 can be configured to alter the display of the associated color in one or more patterns. For example, the LED 112 can output one or more colors in a pattern. The pattern may provide a message to the user based on the different colors in the pattern and/or the timing of the colors. In an aspect, the one or more patterns can be in rhythm with music played via the speaker 114.

In an aspect, the processor 102 can determine an alert state based on the data from the sensor 116. An alert state can be indicative of medical distress of a user. For example, the sensor 116 can provide a heart rate in BPM of the user to the processor 102. The processor 102 can use the heart of the user to determine whether the user is having a medical emergency. If the processor 102 determines that the user has a dangerously elevated heart rate based on the data from the sensor 116, the processor 102 can provide a notification to a user to indicate they are experiencing a medical emergency. The physiological parameter sensing device 100 can transmit one or more of the data and/or the alert state to a computing device via the input/output 110 either wirelessly or physically. In an aspect, the computing device, rather than the processor 102, can determine the alert state. For example, the physiological parameter sensing device 100 can transmit data (e.g., the heart rate of the user) to the computing device. After receiving the data (e.g., the heart rate), the computing device can determine the alert state of the user (e.g., determine if the user is having a medical emergency). The computing device can transmit the alert state to the physiological parameter sensing device 100. After receiving the alert state, the physiological parameter sensing device 100 can output, via one or more of the LED 112 or the speaker 114, a notification to the user to indicate the alert state.

FIG. 2A and FIG. 2B illustrate an example physiological parameter sensing device 200 configured to couple with a computing device (e.g., a smartphone 201). FIG. 2B illustrates the physiological parameter sensing device 200 without being coupled to the smartphone 201. As shown, the physiological parameter sensing device 200 is configured as a device case to encompass a computing device (e.g., a tablet case, a phone case, etc.). As shown in FIG. 2A and FIG. 2B, the physiological parameter sensing device 200 can couple with the smartphone 201 via an input/output connector 203. The input/output connector 203 can couple to the input/output port (not shown) of the smartphone 201. The input/output port of the smartphone 201 and the input/output connector 203 can adhere to any proprietary standard created by a manufacturer. For example, the input/output port of the smartphone and the input/output connector 203 can comprise one or more of a USB connection, a dock connector (e.g., a 20 pin connector, a 24 pin connector, a 30 pin connector, a lightning port connector, etc.), a Portable Digital Media Interface, and the like. The input/output port of the smartphone 201 and the input/output connector 203 can be used to pass power and/or data between the smartphone 201 and the physiological parameter sensing device 200.

The physiological parameter sensing device 200 can comprise a sensor 204 (e.g., the sensor 116 of FIG. 1) that can be configured to sense a physiological parameter. The sensor 204 can comprise, one or more of, a heart rate sensor, a thermal sensor, a pulse oximeter, an electrical sensor, combinations thereof and the like. The sensor 204 can be positioned anywhere on the physiological parameter sensing device 200, such that an accurate sensor reading can be performed. The sensor 204 can be positioned, for example, in a plurality of locations on the physiological parameter sensing device 200 to obtain at least one sensor reading and/or to obtain a plurality of sensor readings. The sensor 204 can be placed in a position where a user is likely to place a finger or a hand. The sensor 204 can provide the sensor reading to the physiological parameter sensing device 200. The physiological parameter sensing device 200 can in turn provide the sensor reading to the smartphone 201 via the input/output connection 203.

In an aspect, an application stored on the smartphone 201 can use the sensor reading to determine a mood state or an alert state of the user. For example, the application can cause the smartphone 201 can determine a value of the physiological parameter, compare the value to a mood index, and select a mood state from the mood index according to the value. Exemplary mood states include, but are not limited to happy, excited, sad, and angry. A color can be associated with each mood state. For example, one or more of yellow, blue, red, and combinations thereof. The physiological parameter sensing device 200 can comprise an LED 205. The application installed on the smartphone 201 can cause the LED 205 to display the associated color. In an aspect, the LED 205 can be configured to alter the display of the associated color in one or more patterns. The one or more patterns can be in rhythm with any played music or can be any other pattern. The LED 205 can be positioned anywhere on the physiological parameter sensing device 200.

The application installed on the smartphone 201 can also determine one or more songs or playlists associated with the mood. The user can specify certain songs and/or playlists, or the application can determine the songs and/or playlists automatically. For example, the one or more songs are selected to play sequentially (e.g., played back) after one another. The songs may be played back in a predetermined order, a random order, or the order can be dynamically determined based on a current mood state or a current physiological parameter of a user. For example, a first song may be selected based on the user having an agitated mood state. The next song may be selected based on the user's mood state after the first song has finished. As an example, if the user is still agitated after the first song, the second song may be a different style (e.g., genre, artist, etc.) than the first song that may do a better job of calming down the user. If the user is calmed down significantly after the first song, the second song may be in the same style as the first song since it had a significant impact on the user's mood state. Thus, the playlist can be determined in a dynamic manner. The smartphone 201 can play the songs and/or the playlist. In an aspect, the songs and/or the playlist can be provided to the physiological parameter sensing device 200, and the physiological parameter sensing device 200 can play the songs and/or playlists. The songs can be stored in a song catalog that is stored on a smartphone associated with a user. The songs can also be streamed on the smartphone or downloaded to the smartphone and stored in the song catalog for playback. The songs, the song catalog, and/or the playlist can be stored on a memory associated with the smartphone.

Figure 3:
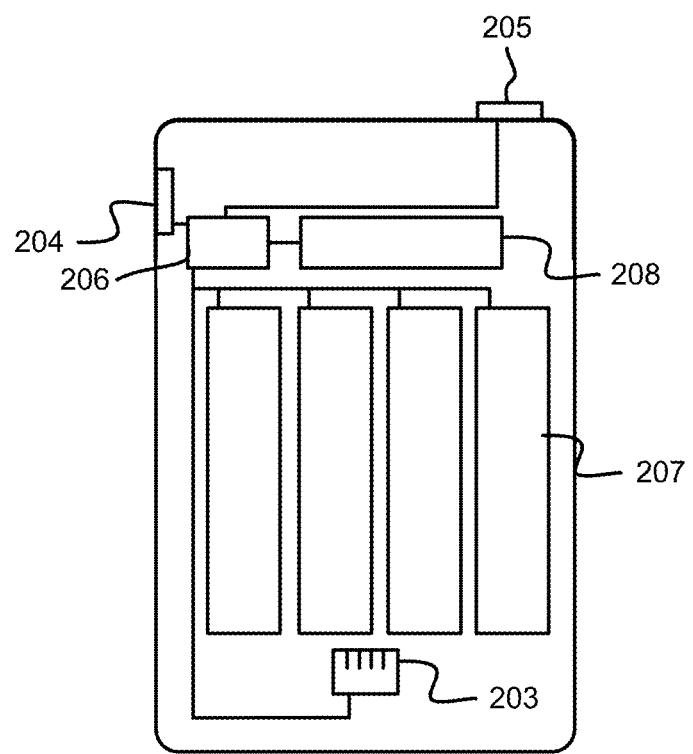
FIG. 3 illustrates another exemplary detachable physiological parameter sensing device.

FIG. 3 illustrates the physiological parameter sensing device 200. In an aspect, the sensor 204 can comprise any sensor disclosed herein or known. The sensor 204 can sense a physiological parameter. The sensed physiological parameter can be provided to a processor 206. The processor 206 can optionally cause the physiological parameter to be stored in a memory 208. The processor 206 can cause the sensed physiological parameter to pass into the input/output connection 203 to a coupled electronic communication device (e.g., the smartphone 201). In an aspect, the physiological parameter sensing device 200 can receive power through the input/output connection 203 from the coupled electronic communication device. For example, the physiological parameter sensing device 200 can receive power from a power supply built into the smartphone 201. In another aspect, the physiological parameter sensing device 200 can receive power through one or more batteries 207. The one or more batteries 207 can be rechargeable. The one or more batteries can comprise a lithium-ion battery (e.g., thin film lithium ion batteries), a lithium ion polymer battery, a nickel-cadmium battery, a nickel metal hydride battery, a lead-acid battery, combinations thereof, and the like. In an aspect, the one or more batteries 207 can exclusively provide power to the physiological parameter sensing device 200 and/or can be configured to provide power to both the physiological parameter sensing device 200 and the smartphone 201. In an aspect, the one or more batteries 207 can provide backup power for the smartphone 201. In another aspect, the one or more batteries 207 can charge one or more batteries internal to the smartphone 201. In another aspect, the one or more batteries 207 can directly power the smartphone 201.

Figure 4:
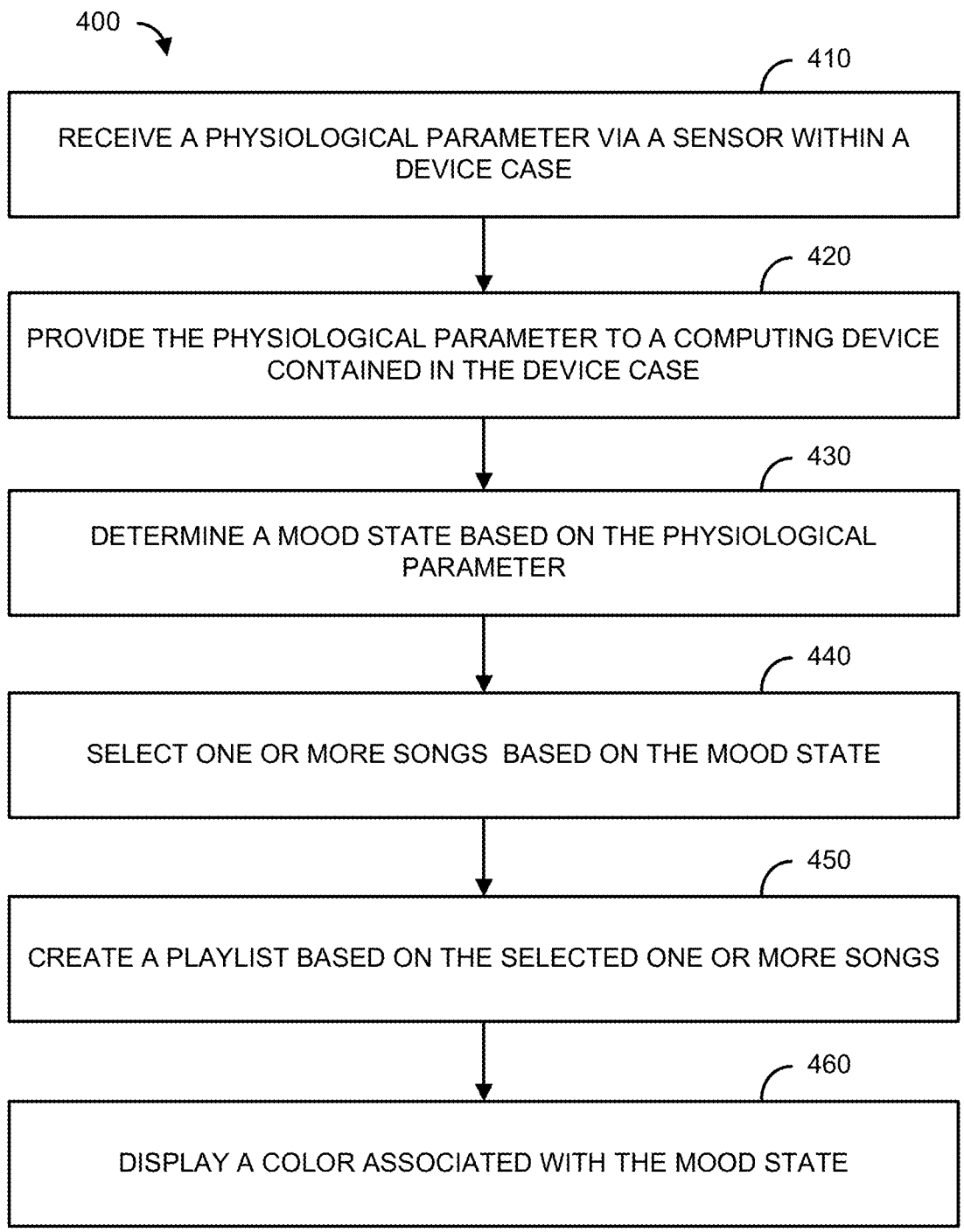
FIG. 4 illustrates an exemplary flowchart.

FIG. 4 illustrates an exemplary method 400. At step 410, a physiological parameter is received (e.g., by the physiological parameter sensing device 100, 200 of FIGS. 1, 2A, and 2B). The physiological parameter can be received from a sensor (e.g., the sensor 116 of FIG. 1) within a device case (e.g., the physiological parameter sensing device of FIGS. 2A and 2B). For example, a user may place an extremity (e.g., a finger, a hand, etc.) on the sensor within the device case. The sensor can then measure the physiological parameter of the user, and provide the measured physiological parameter to a physiological parameter sensing device.

At step 420, the physiological parameter is provided to a computing device (e.g., the smartphone 201 of FIG. 2A) contained within the device case. For example, the physiological parameter sensing device provides the measured physiological parameter to a smartphone contained within the device case. The smartphone can have an application installed on the smartphone that receives the measured physiological parameter.

At step 430, a mood state is determined based on the physiological parameter. For example, the physiological parameter may indicate a heart rate of a user. The heart rate of the user can indicate the mood of the user. As an example, if a person is calm, the user may have a low heart rate. Thus, the mood state of the user is calm based on the low heart rate. Determining the mood state can comprise determining a value of the physiological parameter, comparing the value to a mood index, and selecting a mood from the mood index according to the value. The mood state can be happy, excited, sad, or angry. The mood index can comprise a range of physiological parameters and associated moods.

At step 440, one or more songs are selected based on the mood state. For example, a song can be selected that associates well with the mood state (e.g., a calm song for a calm mood state). As an alternative, the song can be selected that can influence a change in the mood state (e.g., a calm song for an agitated mood state). The one or more songs can be selected from a song catalog associated with the user. As an example, the smartphone can store the song catalog that comprises a plurality of songs. The one or more songs can also be selected from an online service for playback on the smartphone. For example, the one or more songs can be streamed on the smartphone or downloaded to the smartphone and stored in the song catalog for playback.

At step 450, a playlist is created based on the selected one or more songs. For example, the one or more songs are selected to play sequentially (e.g., played back) after one another. The songs may be played back in a predetermined order, a random order, or the order can be dynamically determined based on a current mood state or a current physiological parameter of a user. For example, a first song may be selected based on the user having an agitated mood state. The next song may be selected based on the user's mood state after the first song has finished. As an example, if the user is still agitated after the first song, the second song may be a different style (e.g., genre, artist, etc.) than the first song that may do a better job of calming down the user. If the user is calmed down significantly after the first song, the second song may be in the same style as the first song since it had a significant impact on the user's mood state. Thus, the playlist can be determined in a dynamic manner.

At step 460, a color is displayed (e.g., by the LED 112 of FIG. 1) that is associated with the mood state. For example, the color is displayed by an LED associated with the device case. As another example, the color is displayed by the smartphone contained within the device case. The colors associated with each mood state can be one or more of yellow, blue, green, red, purple, orange, and so forth.

comprising receiving a physiological parameter via a sensor in a device case at 410, providing the physiological parameter to an application installed on a device contained in the device case at 420, determining a mood state based on the physiological parameter, wherein the mood state has an associated color at 430, selecting one or more songs based on the mood state at 440, creating a playlist based on selected one or more songs at 450, and displaying the color associated with the mood state via a light source in the device case at 460.

The method device case can draw power from a power source. The power source can comprise one or more batteries. The one or more batteries can be configured for one or more of, wireless charging (e.g., inductive and/or conductive), supplying a constant DC or pulsed DC power source to a battery being charged, a motion-powered charger, a pulse charger, a solar charger, a wind charger, a Universal Serial Bus (USB) charger, and combinations thereof. The one or more devices can comprise a smartphone, a smart watch, smart lighting, a smart speaker, a tablet, a laptop, and combinations thereof. The physiological parameter can comprise one or more of temperature, heart rate, and blood pressure.

While the methods and systems have been described in connection with preferred embodiments and specific examples, it is not intended that the scope be limited to the particular embodiments set forth, as the embodiments herein are intended in all respects to be illustrative rather than restrictive.

The previous description of the disclosed aspects is provided to enable any person skilled in the art to make or use the present disclosure. Various modifications to these aspects will be readily apparent to those skilled in the art, and the generic principles defined herein can be applied to other embodiments without departing from the spirit or scope of the disclosure. Thus, the present disclosure is not intended to be limited to the embodiments shown herein but is to be accorded the widest scope consistent with the principles and novel features disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:
1. A method comprising:
receiving a physiological parameter via a sensor in a device case;
providing the physiological parameter to an application installed on a device contained in the device case;
determining a mood state based on the physiological parameter, wherein the mood state has an associated color;
selecting one or more songs based on the mood state;

changing, based on selected one or more songs and via the application installed on the device, a song sequence of a playlist comprising the selected one or more songs; and causing a light source integrated into the device case to display the associated color in a pattern associated with the selected one or more songs.

2. The method of claim 1, wherein the device case draws power from a power source.

3. The method of claim 2, wherein the power source comprises one or more batteries.

4. The method of claim 3, wherein the one or more batteries are configured for charging via a motion-powered charger, a pulse charger, a solar charger, a wind charger, or a Universal Serial Bus (USB) charger.

5. The method of claim 1, wherein the device comprises a smartphone, a smart watch, a smart lighting device, a smart speaker, a tablet, or a laptop.

6. The method of claim 1, wherein the physiological parameter comprises one or more of temperature, heart rate, or a blood pressure.

7. The method of claim 1, wherein determining the mood state comprises:
determining a value of the physiological parameter;
comparing the value to a mood index; and
selecting the mood state from the mood index based on the value.

8. The method of claim 7, wherein the mood state is happy, excited, sad, or angry.

9. The method of claim 7, wherein the associated color is one of yellow, blue, green, red, orange, or purple.

10. An apparatus comprising:
a housing configured to receive a device;
a physiological sensor for sensing a physiological parameter of a user, the physiological sensor configured to interact directly with the user and, in response, initiate the sensing;
a light source for displaying a color;
a power source configured to supply power exclusively to the physiological sensor;
an input/output (I/O) device to couple to the device to exchange power and data; and
a processor configured to:
receive the physiological parameter from the physiological sensor,
provide the physiological parameter to an application installed on the device via the I/O device,
receive a command indicating a color,
select, based on the indicated color and via the application, one or more songs,
change, based on the selected one or more songs, a song sequence of a playlist comprising the selected one or more songs, and
cause the light source to display the color in a pattern associated with the selected one or more songs.

11. The apparatus of claim 10, wherein the power source comprises one or more batteries.

12. The apparatus of claim 11, wherein the one or more batteries are configured for charging via a motion-powered charger, a pulse charger, a solar charger, a wind charger, or a Universal Serial Bus (USB) charger.

13. The apparatus of claim 10, wherein the device comprises a smartphone, a smart watch, a smart lighting device, a smart speaker, a tablet, or a laptop.

14. A system comprising:
a first device comprising:
a physiological sensor for sensing a physiological parameter of a user, the physiological sensor configured to interact directly with the user and, in response, initiate the sensing;
a light source for displaying a color;
a first power source configured to supply power exclusively to the physiological sensor;
a first input/output (I/O) device to couple to a second device to exchange one or more of power and data;
a first processor configured to:
receive the physiological parameter via the physiological sensor, and
provide the physiological parameter to an application installed in the first device; and
the second device comprising:
a second power source;
a second I/O device to couple to the first device to exchange one or more of power and data;
a second processor configured to:
determine a mood state based on the physiological parameter, wherein the mood state has an associated color,
select one or more songs based on the mood state,
change, based on the selected one or more songs, a song sequence of a playlist comprising the selected one or more songs; and
provide a command to the first device to cause the light source of the first device to display the associated color in a pattern associated with the selected one or more songs.

15. The system of claim 14, wherein the first power source comprises one or more batteries.

16. The system of claim 15, wherein the one or more batteries are configured for charging via a motion-powered charger, a pulse charger, a solar charger, a wind charger, or a Universal Serial Bus (USB) charger.

17. The system of claim 14, wherein the second device comprises a smartphone, a smart watch, a smart lighting device, a smart speaker, a tablet, or a laptop.

18. The system of claim 14, wherein the playlist is stored on the first device or the second device.

19. The system of claim 14, wherein the mood state is happy, excited, sad, or angry.

20. The system of claim 14, wherein the associated color is one of yellow, blue, green, red, orange, or purple.

* * * * *